United States Patent [19]

Baker et al.

[11] 4,294,261

[45] Oct. 13, 1981

[54] LOGIC-CONTROLLED OCCLUSIVE CUFF SYSTEM

[75] Inventors: Joseph T. Baker, League City; George W. Hoffler, Seabrook; William N. Hursta, League City, all of Tex.

[73] Assignee: The United States of America as represented by the United States National Aeronautics and Space Administration, Washington, D.C.

[21] Appl. No.: 691,647

[22] Filed: Jun. 1, 1976

[51] Int. Cl.³ ............................................. A61B 5/02
[52] U.S. Cl. ................................. 128/691; 128/327; 128/686
[58] Field of Search .................... 128/2.05 A, 2.05 M, 128/2.05 C, 327, 2.05 G, 691, 686

[56] References Cited

U.S. PATENT DOCUMENTS 3,825,008  7/1974  Shook ..................... 128/2.05 A X
3,905,354  9/1975  Cichowsky ............... 128/2.05 M
4,027,662  6/1977  Lee ........................... 128/2.05 A

OTHER PUBLICATIONS

Schulze et al., Southwestern Inst. of Electrical and Electronics Engr. Conf. Record, (4–1968), pp. 17F1–17F5.

Primary Examiner—Michael H. Thaler
Attorney, Agent, or Firm—Marvin J. Marnock; John R. Manning; Marvin F. Matthews

[57] ABSTRACT

The occlusive cuff system of this invention comprises a pressure cuff and a source of regulated compressed gas feeding the cuff through an electrically-operated fill valve. An electrically-operated vent valve vents the cuff to the ambient pressure. The fill valve is normally closed and the vent valve is normally open. In response to an external start signal, a logic network opens the fill valve and closes the vent valve, thereby starting the pressurization cycle and a timer. A pressure transducer continuously monitors the pressure in the cuff. When the transducer's output equals a selected reference voltage, a comparator causes the logic network to close the fill valve. The timer, after a selected time delay, opens the vent valve to the ambient pressure, thereby ending the pressurization cycle.

4 Claims, 2 Drawing Figures

LOGIC-CONTROLLED OCCLUSIVE CUFF SYSTEM

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435, 45 U.S.C. 2457).

BACKGROUND OF THE INVENTION

Many blood flow experiments employ hand pumping techniques for inflating occlusion cuffs. Blood flow information obtained from using hand-pumping techniques is frequently inaccurate or if accurate is hard to interpret due to a considerable range of possible variations. The need therefore exists for equipment which would automatically inflate and deflate the cuffs to preset pressures and for preset time durations. Such automatic cuff inflation devices as are known may be adequate for large size laboratories. For small laboratories or for specialized environments such as exist, for example, in space flights, it is required that such automatic devices be simple to operate, be suitable for carrying out blood flow experiments in connection with instrumentation and power supplies used in space flights, and have controls that are easily accessible to the astronaut whose blood flow is being measured. Such controls include means for selecting the cuff maximal fill pressure, the duration of maintaining this fill pressure, and the time of initiating the inflation-deflation cycle in order to optimize function for different individuals.

It is a main object of this invention to provide logic-controlled valves in an occlusive cuff system which is characterized by extremely accurate pressure-time cycles that meet all the above-mentioned desiderata and others which will become apparent from the following detailed description of the invention.

SUMMARY OF THE INVENTION

A normally-closed fill valve couples a source of regulated compressed gas to the cuff. A normally-closed vent valve is maintained energized and therefore open to insure zero pressure in the cuff. A logic network controls the opening and closing times of the valves. The network includes logic circuitry, a pressure transducer, a comparator, and a timer. In response to an external start signal, the network starts a pressurization cycle of the cuff by opening the fill valve, activating the timer, and closing the vent valve. The pressure transducer continuously monitors the cuff's pressure. The output of the transducer is compared with a preset reference voltage corresponding to the desired pressure in the cuff. When the transducer's output equals the reference voltage, the comparator's output will cause the logic circuitry to close the fill valve. With both valves closed, the cuff remains pressurized. After a selected time interval, the timer will cause the vent valve to open, thereby depressurizing the cuff. The system is now ready to start a new cycle of operation.

In a modified embodiment, the system will accept the output of an electrocardiogram (ECG) trigger circuit which starts the logic network at a preselected time after the peak of the ECG R-wave.

DESCRIPTION OF A PREFERRED SYSTEM

General Description of the System

Figure 1:
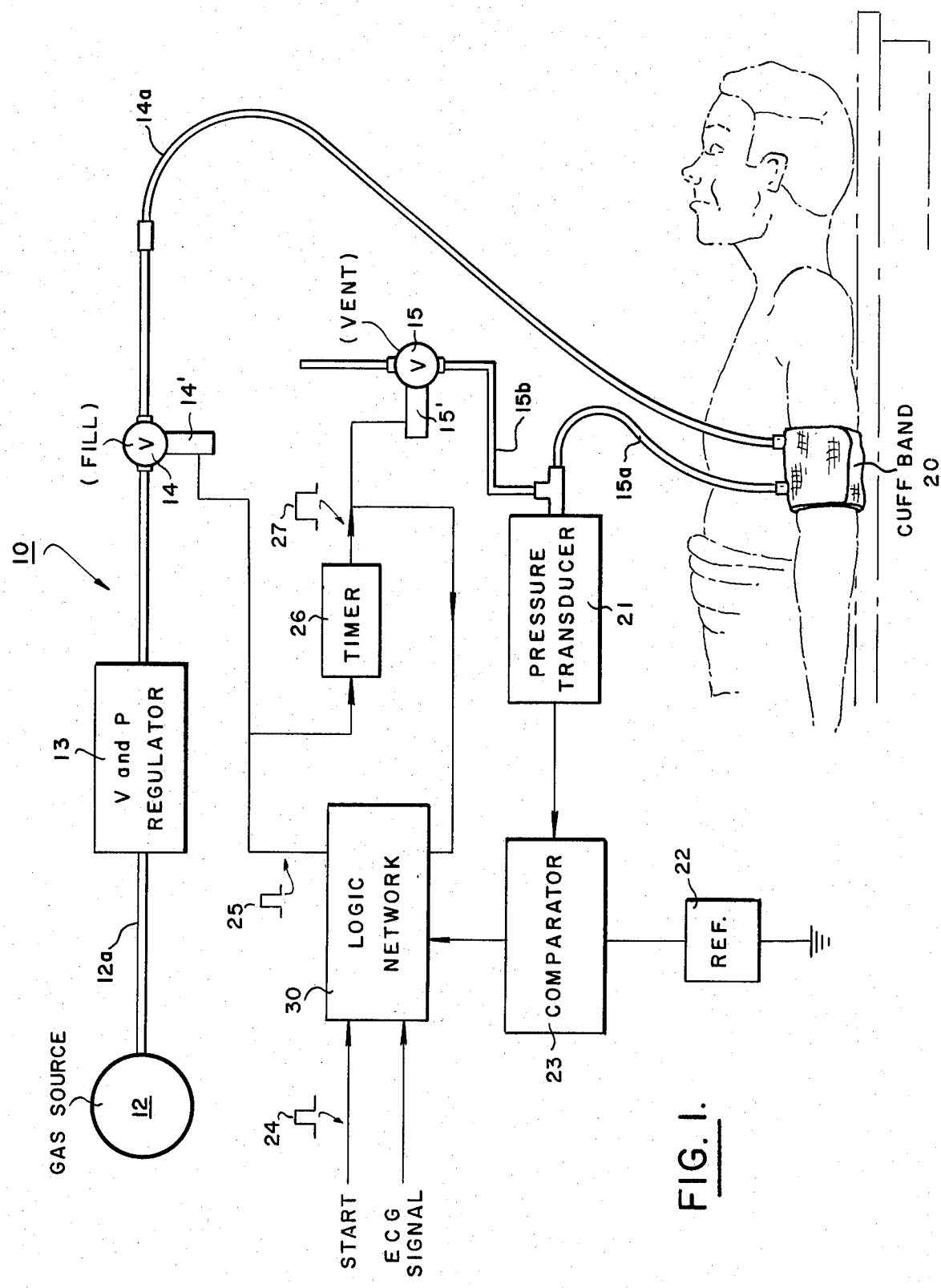
FIG. 1 is a generalized block diagram of the pneumatic and electronic parts in the occlusive cuff system of this invention.

The cuff controller system 10 (FIG. 1) of this invention comprises a source 12 of gas having a maximum pressure of about 300 psi. The pneumatic source 12 is coupled to a conventional cuff 20 through a conduit 12a a volume-and-pressure regulator 13, and a fill valve 14 installed in a suitable conduit 14a. A vent valve 15 installed in suitable conduits 15a and 15b vents the cuff to the ambient atmosphere. Valves 14 and 15 are electrically operated and for convenience are represented as being solenoid-operated valves. Thus valves 14, 15 have solenoids 14', 15', respectively.

A transducer 21 continuously monitors the pressure in cuff 20 and produces an output electric signal which is fed to one input of a voltage comparator 23. A reference voltage source 22 feeds the other input to the comparator.

The output of comparator 23 constitutes one input to a logic network, generally designated as 30. The other input to network 30 is a start signal 24. An ECG signal can also start the logic network 30 together with the start signal 24. The logic network 30 when started (1) produces a "fill" signal 25 which is simultaneously applied to solenoid 14' and to a timer 26, and (2) produces a signal which changes a normally-existing vent signal 27 that is applied to solenoid 15'.

General Operation of System 10

In operation, regulator 13 controls the volume and pressure of the gas flowing into occlusive cuff 20. Valves 14 and 15 are normally closed when de-energized. Prior to the start of a pressurization cycle, solenoids 14' is deenergized (valve 14 closed) and solenoid 15' is energized (valve 15 open) to insure that the pressure in cuff 20 is equal to the ambient pressure. In response to the start signal 24 and/or the ECG signal, logic network 30 starts the fill signal 25 which energizes solenoid 14' and opens valve 14.

The fill signal 25 is also applied to timer 26 which changes the vent signal 27 thereby closing valve 15. With valve 14 open and valve 15 closed, the pressurization of cuff 20 is made possible.

Regulated gas at about 100 psi at a nominal flow rate of about 5 cubic feet per minute pressurizes cuff 20 to a preset pressure determined by the reference voltage 22. The pressure transducer 21 continuously monitors the pressure in cuff 20 and when its output is equal to the reference voltage 22, the output of comparator 23 changes and this change causes network 30 to end the fill signal 25 whereby valve 14 closes. Valve 14 holds the pressure in cuff 20.

After the end of a preset time interval, timer 26 restores the vent signal 27 to its original condition which causes solenoid 15' to energize and valve 15 to open. With valve 14 closed, the opening of valve 15 depressurizes cuff 20 and prepares the cuff for another pressurization cycle.

DETAILED DESCRIPTION OF LOGIC NETWORK 30

Figure 2:
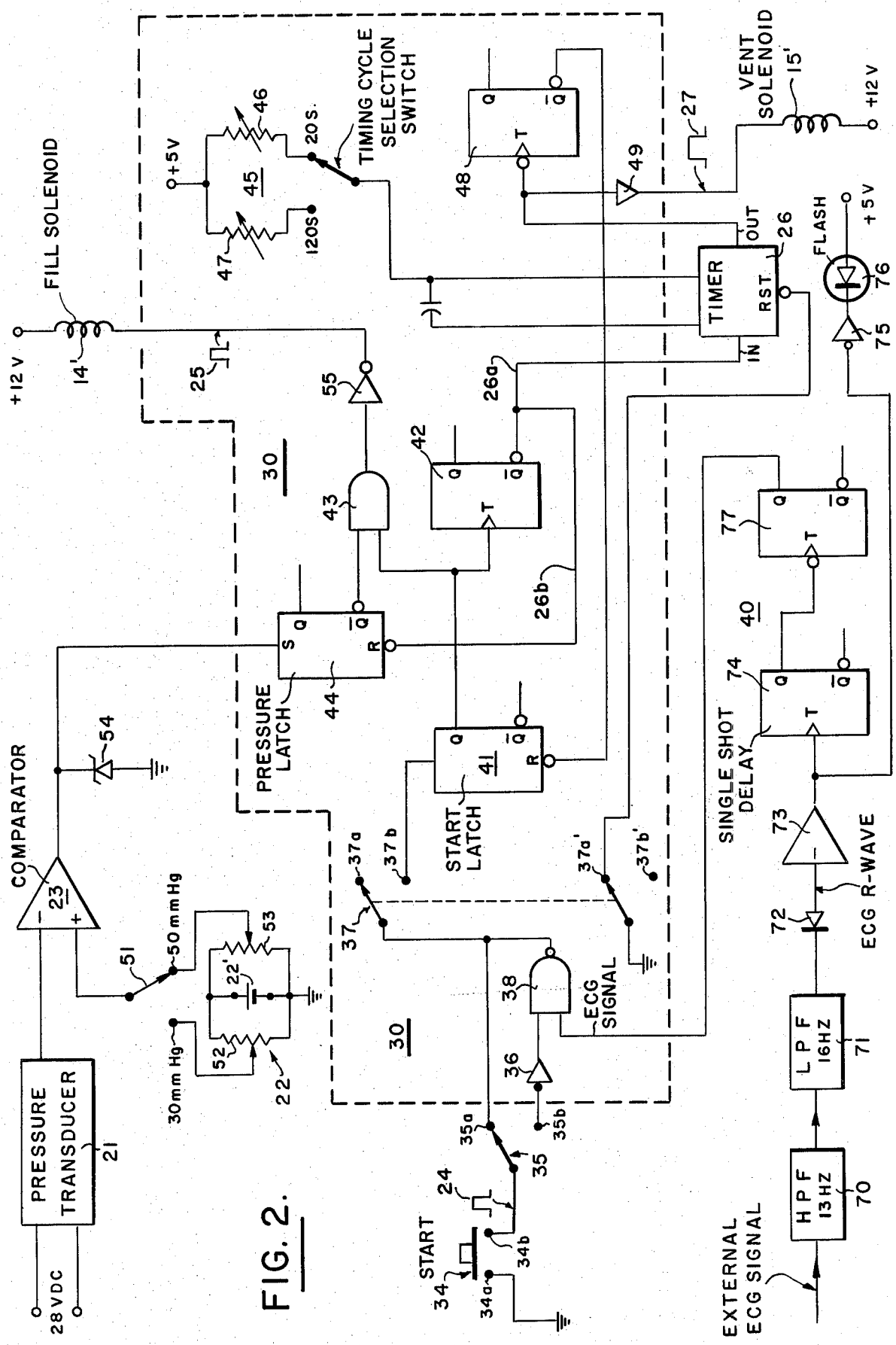
FIG. 2 is a schematic diagram of the electronics shown in FIG. 1.

In both FIGS. 1 and 2 and in the description of network 30, the same reference characters are used to facilitate the understanding of the invention.

The start signal 24 is produced by a start push button 34 having one contact 34a connected to ground and the other contact 34b connected to a single-pole, double-throw switch 35. Contact 35a of switch 35 is connected to a double-pole, double-throw reset switch 37 which in its reset condition makes contact with terminals 37a and 37a', and in its normal condition makes contact with terminals 37b and 37b'. Switch 35 can also be moved to contact 35b which is connected through an inverter 36 to one input of a NAND gate 38. The ECG signal which is derived from a remote ECG trigger circuit, generally designated as 40, is supplied to the other input of NAND gate 38. Contact 37b is connected to a start latch 41 whose output is simultaneously applied to a one-shot multivibrator 42 and to an AND gate 43. The inverted output of multivibrator 42 is simultaneously applied by conductor 26a to the input of timer 26 and by conductor 26b to the reset terminal of a pressure latch 44.

Timer 26 can produce two preset time intervals depending on the position of a timing-cycle, selection switch 45 which engages either variable potentiometer 46 or variable poteniometer 47. Variable potentiometer 46 produces a 20 sec. delay, and variable potentiometer 47 produces a 120 sec. delay.

The output of timer 26 is simultaneously applied to a one-shot multivibrator 48 and to a driver 49 which changes the vent signal 27 that is normally applied to solenoid 15'. The inverted output of multivibrator 48 is applied to the reset terminal of the start latch 41.

The pressure transducer 21 continuously monitors the pressure existing in cuff 20 (FIG. 1) and produces a DC signal which is directly proportional to the monitored pressure. The DC signal is applied to the inverting input of a differential amplifier or comparator 23 whose non-inverting input is connected to a pressure selector switch 51 which can select either a variable voltage divider 52 (30 mmHg) or a variable voltage divider 53 (50 mmHg).

A DC reference source 22' is coupled across voltage dividers 52, 53 which are connected in parallel. The output of comparator 23, which is normally maintained at 3.6 volts by a Zener diode 54, is supplied to the set terminal of pressure latch 44. The inverted output of pressure latch 44 is applied to the other input terminal of the AND gate 43. The output of AND gate 43 is connected to an inverting driver 55 which produces the fill signal 25 to the solenoid 14'.

OPERATION OF LOGIC NETWORK 30

The start signal 24 to network 30 is produced by depressing the start push-button 34. Switch 35 is then in the position as shown in FIG. 2 and switch 37 contacts terminals 37b and 37b'. Prior to the pressurization of cuff 20, solenoid 14' is de-energized (fill signal 25 is off and valve 14 is closed) and solenoid 15' is energized by the vent signal 27 (valve 15 is open). In response to the start signal 24 and to the output of comparator 23, network 30 will control its two output signals 25 and 27.

FILL SIGNAL 25

Upon the application of the start signal 24, the start latch 41 sets, its output goes high, thereby triggering the one-shot 42 whose inverted output starts timer 26 and resets pressure latch 44 whose inverted output goes high. The outputs of start latch 41 and of pressure latch 44 are andgated by AND gate 43 which causes driver 55 to produce the fill signal 25 that energizes solenoid 14' and opens valve 14. Pressure is now being admitted into cuff 20 very rapidly and the pressure therein is being continuously monitored by the pressure transducer 21. When the output of pressure transducer 21 becomes equal to the reference voltage selected by switch 51, the output of comparators 23 drops from 3.6 volts to 0 volts which sets the pressure latch whose inverted output goes low, making the output of AND gate 43 go low, which makes the fill signal 25 go low, thereby de-energizing solenoid 14' and closing valve 14. The cuff is now in its pressure holding mode.

VENT SIGNAL 27

When the output of one-shot multivibrator 42 set timer 26, its output went low causing the non-inverting driver 49 to make the vent signal 27 go low, thereby de-energizing solenoid 15' and closing vent valve 15 simultaneously with the opening of the fill valve 14. At the end of the preselected time interval (20 or 120 seconds), as determined by the position of the timing-cycle, selection switch 45, the output of timer 26 goes low which makes the vent signal 27 from the output of driver 49 go high, thereby energizing solenoid 15' and opening vent valve 15 to the ambient pressure. When the output of timer 26 goes high, the one-shot 48 is triggered and its inverted output resets the start latch 41. The logic network 30 is now again ready to start a new pressurization cycle.

When the reset switch 37 is moved to make contact with its terminals 37a and 37a', the timer's output is forced and held low, thereby causing the energization of solenoid 15' and the opening of vent valve 15. In addition, the input to the start latch 41 is disconnected from the start button 34, thereby preventing the unintentional setting of the start latch 41.

THE ECG TRIGGER CIRCUIT 40

The remote ECG trigger circuit 40 permits the start of logic network 30 at a preselected time after the peak of the ECG R-wave. The timer 26 allows the system 10 to occlude venous return at a highly reproducible point in the ECG waveform, if the heart's rate is relatively constant. The ECG trrigger circuit 40 receives an external ECG signal derived from an electro-cardiograph (not shown). The ECG signal is first filtered by a 13 Hz high-pass filter 70 and then by a 16 Hz low-pass filter 71. The net effect of this filtering is to filter out substantially everything except the R peak of the ECG waveform. The highly filtered R-peak is then detected by a pulse detector 74 which outputs a square wave pulse to an inverting amplifier 73. The output of inverting amplifier 73 is applied to a one-shot multivibrator 74 and to a driver 75 which drives a light-emitting diode or flasher 76 to indicate proper circuit operation. The one-shot multivibrator 74 delays the pulse by a fixed or adjustable time delay, say 100 ms. After the desired time delay, the signal goes to a second one-shot multivibrator 77 whose output is connected to NAND gate 38. When the start push button switch 34 is depressed, and if the manual selector switch 35 makes contact with its terminal 35b, the signal from one-shot multivibrator 77 will start the pressurization cycle.

By altering the delay of the one-shot multivibrator 74, the initiation of the pressurization cycle in cuff 20 can be placed anywhere within the ECG waveform.

ADVANTAGES OF SYSTEM 10

It will be appreciated from the above description that the system 10 of this invention provides accurate and highly reproducible pressurization cycles of the occluding cuff 20 with extremely accurate timing. The system has easily adjustable pressure and timing cycles to meet the needs of specific individuals. The particular timing cycle can be easily selected by switch 45. Similarly, the pressure level in cuff 20 can be easily selected by switch 51. The network 30 can also be initiated and the selected pressurization cycle controlled by an externally supplied ECG signal. This feature provides consistent triggering of the pressurization cycle during the heat pumping cycle. The remote ECG trigger circuit 40 can be used or disabled by merely operating manual switch 35.

What is claimed is:

1. A cuff system for occluding venous return from a limb, comprising:

a pressure cuff;

a source of pressurized gas;

means including a solenoid-operated fill valve for selectively coupling said gas source with said cuff, said fill valve being opened in response to a high level energizing electrical fill signal which energizes the solenoid associated with said fill valve and being closed in response to the application of a low level electrical signal to said solenoid-operated fill valve;

regulator means for controlling the pressure and volume of gas flowing from said source when coupled to said cuff;

means including a solenoid-operated vent valve for venting said cuff to the ambient atmosphere, said vent valve being closed in response to application of a low level electrical signal which deenergizes the solenoid associated with said vent valve and said vent valve being opened in response to application of a high level electrical signal which energizes the vent solenoid;

means for supplying a high level energizing electrical fill signal to said solenoid-operated fill valve to open said fill valve and maintain the fill valve in open condition whereby the cuff receives gas from said pressurized source;

means including a timer means instantly operative in response to said fill signal for producing a low level deenergizing close vent signal for a predetermined period of time and applying said low level close vent signal to said vent valve to close said vent valve through said time period;

a pressure transducer fluidly coupled with said cuff, said transducer measuring the fluid pressure in said cuff and generating a transducer output electrical voltage signal proportional to said pressure;

a source of reference voltage;

means operatively associated with said pressure transducer and said reference voltage source for terminating said high level energizing electrical fill signal and applying a second low level electrical signal to said solenoid-operated fill valve to close said fill valve when the ratio between said transducer electrical output voltage signal and said reference voltage signal reaches a predetermined value whereby said cuff is in a pressure holding condition while the vent remains closed; and means responsive to the termination of said low level deenergizing close vent signal at the end of said time period to energize said solenoid-operated vent valve to open condition and thereby depressurize said cuff; said system further comprising:

an AND gate, a pressure latch, a start latch, each one of said latches having a set, reset, and output terminals, the output of said pressure latch being coupled to one input of said AND gate, the output of said start latch being coupled to the other input of said AND gate, means coupling the output of said start latch to the input of said timer and to the reset terminal of said pressure latch, means coupling the output of said timer to the reset terminal of said start latch, means coupling the output of said AND gate to said fill valve; and said system adapted to start a pressurization cycle upon the application of a start signal to the set terminal of said start latch.

2. The system of claim 1 and further comprising:

means coupling an external signal to said set terminal of said start latch.

3. The system of claim 2 and further including an electrocardiogram trigger circuit for providing said external signal, said trigger circuit comprising:

a filter means receiving an ECG signal, a detector coupled to the output of said filter means, and a time delay network coupled to the output of said detector.

4. The system of claim 3 wherein said filter means comprises a high-pass filter in tandem with a low-pass filter, said ECG signal being applied to said high-pass filter.

* * * * *